United States Patent [19]

Doyle et al.

[11] Patent Number: 5,302,388

[45] Date of Patent: Apr. 12, 1994

[54] CONTROL OF CAMPYLOBACTER JEJUNI COLONIZATION

[75] Inventors: Michael P. Doyle, Peachtree City, Ga.; Jean L. Schoeni, Lake Mills, Wis.

[73] Assignee: Wisconsin Alumni Research Foundation, Madison, Wis.

[21] Appl. No.: 791,741

[22] Filed: Nov. 13, 1991

[51] Int. Cl.$^5$ .................. C12N 1/12; C12N 1/20
[52] U.S. Cl. .................. 424/93 C; 424/930; 435/252.1; 435/252.4; 435/252.8; 435/822; 435/849; 435/852; 426/61
[58] Field of Search .......... 435/252.1, 252.4, 252.8, 435/822, 849, 852; 424/93 C, 93 D, 93 R; 426/61

[56] References Cited

U.S. PATENT DOCUMENTS

| | | | |
|---|---|---|---|
| 3,857,971 | 12/1974 | Abdo et al. | 424/93 C |
| 4,404,186 | 9/1983 | Ron | 435/252.8 |
| 4,657,762 | 4/1987 | Mikkola et al. | 424/93 C |
| 4,761,372 | 8/1988 | Maas et al. | 435/252.8 |

FOREIGN PATENT DOCUMENTS 43918 10/1965 France .................. 424/93 C

OTHER PUBLICATIONS

Cowen, et al.; *Bergey's Manual of Determinative Bacteriology*, 8th ed., 1974; pp. 290-298, 321-324.

Boyd, R. F. et al.; *Basic Medical Microbiology*, 3rd ed. 1986, p. 520.

Baker, R. C., M. D. C. Paredes, and R. A. Qureshi, 1987, "Prevalence of *Campylobacter jejuni* in eggs and poultry meat in New York State" *Poultry Sci.* 66: 1766-1770.

Beery, J. T., M. B. Hugdahl, and M. P. Doyle, 1988, "Colonization of gastrointestinal tracts of chicks by *Campylobacter jejuni*" *Appl. Environ. Microbiol.* 54: 2365-2370.

Blaser, D. N. Taylor, and R. A. Feldman, 1983, "Epidemiology of *Campylobacter jejuni* infections," *Epidemiol. Rev.* 5:157-176.

Brouwer, R., M. J. Mertens, T. H. Siem, and J. Katachaki, 1979, "An explosive outbreak of *Campylobacter* enteritis in soliders." *Antonie van Luewenhook J. Microbiol.* 45:517-519.

Butzler, J. P. and M. B. Skirrow, 1979, "*Campylobacter* enteritis." *Clin. Gastroenterol.* 8: 737-765.

Deming, M. S., R. V. Tauxe, P. A. Blake, S. E. Dixon, B. S. Fowler, T. S. Jones, E. A. Lockamy, C. M. Patton, and R. O. Sikes, 1987, "*Campylobacter* enteritis at a university: transmission from eating chicken and from cats," *Am. J. Epidemiol.* 126: 526-534.

Doyle, M. P. and D. J. Roman, 1982, "Recovery of *Campylobacter jejuni* and *Campylobacter coli* from foods by selective enrichment," *Appl. Environ. Microbiol.* 43: 1343-1353.

Grant, I. H., N. J. Richardson, and V. D. Bokkenheuser, 1980, "Broiler chickens as a potential source of *Campylobacter* infections in humans," *J. Clin. Microbiol.* 11: 500-510.

Harris, N. V., D. Thompson, D. C. Martin, and C. M. Nolan, 1986, "A survey of *Campylobacter* and other bacterial contaminants of pre-market chicken and retail poultry and meats, King County, Wash." *Am. J. Publ. Health* 76: 401-406.

Harris, N. V., N. S. Weiss, and C. M. Nolan, 1986, "The role of poultry and meats in the etiology of *Campylobacter jejuni/coli* enteritis," *Am. J. Publ. Health* 76: 407-411.

Hood, A. M., A. D. Pearson, and M. Shahamat, 1988, "The extent of surface contamination of retail chickens with *Campylobacter jejuni* serogroups," *Epidemiol. Infect.* 100: 17-25.

(List continued on next page.)

*Primary Examiner*—Douglas W. Robinson
*Assistant Examiner*—Kristin Larson
*Attorney, Agent, or Firm*—Ross & Stevens

[57] ABSTRACT

New strains of microorganisms producing anti-Campylobacter metabolites have been identified which have the ability to utilize mucin as a sole substrate for growth and the ability to reduce and/or inhibit the incidence of *Campylobacter jejuni* colonization in poultry.

20 Claims, 1 Drawing Sheet

OTHER PUBLICATIONS

Hopkins, R. S. and A. S. Scott, 1983, "Handling raw chickens as a source for sporadic *Campylobacter jejuni* infections." *J. Infect. Dis.* 148: 770.

Hopkins, R. S., R. Olmsted, and G. R. Istre, 1984, "Endemic *Campylobacter jejuni* infection in Colorado: identified risk factors," *Am. J. Publ. Health* 74: 249–250.

Howard, B. J. (ed.), 1987, *Clinical and Pathogenic Microbiology*, C. V. Mosby, St. Louis, Mo., pp. 299–301, 304–307, 440.

Hugdahl, M. B., J. T. Beery, and M. P. Doyle, 1988, "Chemotactic behavior of *Campylobacter jejuni*," *Infect. Immun.* 51: 536–546.

Humphrey, T. J. D. G. Lanning, and G. C. Mead, 1989, "Inhibition of *Campylobacter jejuni* in vitro by broiler chicken cecal contents," *Vet. Rec.* 125: 272–273.

Istre, G. R., M. J. Blaser, P. Shillam, and R. S. Hopkins, 1984, "*Campylobacter* enterities associated with undercooked barbecued chicken," *Am. J. Publ. Health* 74: 1265–1267.

Kaino, K., H. Hayashidani, K. Kaneko, and M. Ogawa, 1988, "Intestinal colonization of *Campylobacter jejuni* in chickens," *Jpn. J. Vet. Sci.* 50: 489–494.

Kinde, H., C. A. Genigeorgis, and M. Pappainou, 1983, "Prevalence of *Campylobacter jejuni* in chicken wings," *Appl. Environ. Microbiol.* 45: 1116–1118.

Lee, A., J. L. O'Rourke, P. J. Barrington, and T. J. Trust, 1986, "Mucus colonization as a determinant of pathogenicity in intestinal infection by *Campylobacter jejuni*: a mouse cecal model," *Infect. Immun.* 51: 536–546.

MacFaddin, J. F. 1980, *Biochemical Tests for Identification of Medical Bacteria*, 2nd ed. Williams and Wilkins, Baltimore, Md., pp. 346, 360–369, 411–438.

Norkrans, G., and A. Svedhem, 1982, "Epidemiological aspects of *Campylobacter jejuni* enteritis," *J. Hyg.* 89: 163–170.

Oosterom, J., S. Notermans, H. Karman, and G. B. Engels, 1983, "Origin and prevalence of *Campylobacter jejuni* poultry processing," *J. Food. Prot.* 46: 339–344.

Prescott, J. F., and C. W. Bruin-Mosch, 1981, "Carriage of *Campylobacter jejuni* in healthy and diarrhetic animals," *Am. J. Vet. Res.* 42: 164–165.

Rettig, P. J. 1979, "*Campylobacter* infections in human beings," *J. Pediatr.* 94: 855.

Rosenfield, J. A., G. J. Arnold, G. R. Savey, R. S. Archer, and W. H. Woods, 1985, "Serotyping of *Campylobacter jejuni* from an outbreak of enteritis implicating chicken," *J. Infect.* 11: 159–165.

Sanyal, S. C., K. M. N. Islam, P. K. B. Neogy, P. Speelman, and M. I. Huq, 1984, "*Campylobacter jejuni* diarrhea model in infant chickens," *Infect. Immun.* 43: 931–936.

Shanker, S., A. Lee, and T. C. Sorrell, 1986, "*Campylobacter jejuni* in broilers: the role of vertical transmission," *J. Hyg.* 96: 153–159.

Shanker, S., A. Lee, and T. C. Sorrell, 1988, "Experimental colonization of broiler chicks with *Campylobacter jejuni*," *Epidemiol. Infect.* 100: 27–34.

Shanker, S., A. Lee, and T. C. Sorrell, 1990, "Horizontal transmission of *Campylobacter jejuni* amongst broiler chicks: experimental studies." *Epidemiol. Infect.* 104: 101–110.

Soerjadi, A. S., G. H. Snoeyenbos, and O. M. Weinack, 1982, "Intestinal colonization and competitive exclusion of *Campylobacter fetus* subsp. *jejuni* in young chicks." *Avian Dis.* 26: 520–524.

Soerjadi-Liem, A. S., G. H. Snoeyenbos, and O. M. Weinack, 1984, "Comparative studies on competitive exclusion of three isolates of *Campylobacter fetus* subsp. *jejuni* in chickens by native gut microflora," *Avian Dis.* 28: 139–146.

Stern, N. J. and S. U. Kazmi, 1989, "*Campylobacter*," pp. 71–110, In M. P. Doyle (ed.), *Foodborne bacterial pathogens*, Marcel Dekker, New York.

Stern, N. J. and J. S. Bailey, L. C. Blankenship, N. A. Cox, and F. McHan, 1988, "Colonization characteristics of *Campylobacter jejuni* in chick ceca," *Avian Dis.* 32: 330–334.

Stern, N. J., M. P. Hernandez, L. Blankenship, K. E. Deibel, S. Doores, M. P. Doyle, H. Ng, M. D. Pierson, N. J. Sofos, W. H. Sveum, and D. C. Westhoff, 1985, "Prevalence and distribution of *Campylobacter jejuni* and *Campylobacter coli* in retail meats," *J. Food Prot.* 48: 595–599.

Varga, J., B. Mezes, and L. Fodor, 1990, "Serogroups of *Campylobacter jejuni* from man and animal," *J. Vet. Med.* B37: 407–411.

Wempe, J. M., C. A. Genigeorgis, T. B. Farver, and H. I. Yusufri, 1983, "Prevalence of *Campylobacter jejuni* in two California chicken processing plants," *Appl. Environ. Microbiol.* 45: 355–359.

FIG. 1

CONTROL OF CAMPYLOBACTER JEJUNI COLONIZATION

FIELD OF THE INVENTION

The present invention relates to novel microorganisms, and particularly to strains of cecal-colonizing bacteria which have the ability to reduce the colonization of *Campylobacter jejuni* in poultry. The present invention is also directed to a process for providing the microorganisms to poultry in effective dosages.

REFERENCE TO CITATIONS

A full bibliography of the references cited in the present application is located in the section prior to the claims.

BACKGROUND OF THE INVENTION

*Campylobacter jejuni* (*C. jejuni*) is recognized as the leading cause of acute bacterial gastroenteritis in the United States and many developed countries (Blaser, M. J., et al., 1983; Butzler, J. P., et al., 1979; Rettig, P. J., 1979). A variety of wild and domestic animals are intestinal carriers and are recognized reservoirs of the organism (Soerjadi-Liem, A. S., et al., 1984). Although these animals often excrete $10^4$–$10^8$ *C. jejuni* per gram of feces, they are typically asymptomatic (Grant, I. H., et al., 1980; Oosterom, J., et al., 1983; Wempe, J. M., et al., 1983). Surveys reveal between 30 and 100% of poultry carry the organism (Grant. I. H., et al., 1980; Oosterom, J., et al., 1983; Prescott, J. F., et al., 1981; Shanker, S., et al., 1986; Shanker, S., et al., 1990; Stern, N. J., et al., 1988; Stern, N. J., et al., 1985; Varga. J., et al., 1990; Wempe, J. M., et al., 1983). Serotypes of *C. jejuni* frequently involved in human infection are often the same as those isolated from poultry. Investigations of outbreaks and sporadic cases of Campylobacter enteritis have revealed poultry is a principal vehicle of illness (Brouwer, R., et al., 1979; Deming, M. S., et al., 1987; Grant, I. H., et al., 1980; Harris, N. V., et al., 1986; Hopkins, R. S., et al., 1983; Hopkins, R. S., et al., 1984; Istre, G. R., et al., 1984; Norkrans, G., et al., 1982; Rosenfield, J. A., et al., 1985).

*C. jejuni* is disseminated from live birds to dressed carcasses and poultry parts during processing (Baker, R. C., et al., 1987). Results of a large national survey of retail meats and poultry revealed that *C. jejuni* contaminated 30% of fresh chickens and only 5.1% of red meats (Stern, N. J., et al., 1985). Similarly, Harris et al. (1986) reported *C. jejuni/coli* contamination of 23% of 862 retail chickens but infrequent contamination of retail turkey, beef, and pork. Studies by Kinde et al. (1983) revealed up to 83% of retail chickens were contaminated with *C. jejuni*. A prospective case-control study by the Seattle-King County Public Health Department revealed that approximately half of the cases of Campylobacter enteritis were associated with ingestion of poultry products (Rettig, P. J., 1979). Deming et al. (1987) identified consumption of chicken or contact with cats or kittens as the major risk factors involved in sporadic cases of Campylobacter enteritis, among college students, implicating chicken as a vehicle in about 70% of the cases. Hence, poultry appears to be the major vehicle of Campylobacter enteritis in the United States.

Studies of chicks perorally inoculated with *C. jejuni* reveal that the birds are readily colonized by *C. jejuni* (Beery, J. T., et al., 1988; Kaino, K., et al., 1988; Sanyal, S. C., et al., 1984; Shanker, S., et al., 1988; Soerjadi. A. S., et al., 1982; Soerjadi-Liem, A. S., et al., 1984; Stern, N. J., et al., 1989), with the ceca being the primary sites of localization (Beery, J. T., et al., 1988). Histologic examination of these ceca revealed campylobacters localize in the lumen of mucus-filled crypts. Campylobacters appear to colonize the crypt mucus without attaching to the microvilli (Beery, J. T., et al., 1988). Hugdahl et al. (1988), studying the chemotactic behavior of *C. jejuni*, observed that the organism is attracted to mucin, and specifically to L-fucose which is a component of mucin. Mucin, a high molecular weight glycoprotein, is the principal constituent of mucus. In addition to its chemoattractant properties, mucin also can be utilized by *C. jejuni* as a sole substrate for growth (Hugdahl, M. B., et al., 1988).

Before the present invention, it had been difficult to isolate any active ingredients which combat the colonization of *C. jejuni* in poultry. Because of the detrimental effects of *C. jejuni* on humans resulting from transmission by poultry, there is a definite need for an effective treatment and control of the colonization of *C. jejuni* in poultry.

SUMMARY OF THE INVENTION

Accordingly, the present invention is directed to a process for reducing or inhibiting the colonization of *C. jejuni* in poultry. The process includes administering an effective amount of at least one cecal-colonizing strain of bacteria, which strain produces anti-Campylobacter metabolites, in combination with a carrier, to the poultry.

The present invention is also directed to new strains of cecal-colonizing bacteria isolated from *Campylobacter jejuni* (*C. jejuni*)-free laying hens, which have been screened for the ability to produce anti-Campylobacter metabolites. The particular strains are advantageous for their ability to (1) colonize in ceca, and (2) utilize mucin as a sole substrate. The identified strains include *Klebsiella pneumoniae* strain 23, *Citrobacter diversus* strain 22, and *Escherichia coli* (O13:H−) strain 25. The strains, alone or in combination, were found to substantially reduce the incidence of *C. jejuni* colonization in chicks.

Accordingly, the present invention is directed to a process for reducing or inhibiting the colonization of *C. jejuni* in poultry comprising administering an effective amount of at least one cecal-colonizing strain of bacteria, which strain produces anti-Campylobacter metabolites, in combination with a carrier, to the poultry.

The present invention is further directed to an anti-*Campylobacter jejuni*-colonizing poultry feed additive comprising a poultry feed material and, as the active ingredient, an effective amount of at least one cecal-colonizing strain of bacteria, which produces anti-Campylobacter metabolites, to provide upon addition to a conventional poultry feed, a poultry feed containing an effective quantity of anti-Campylobacter metabolites to inhibit the colonization of *Campylobacter jejuni* in poultry.

The present invention is further directed to an anti-*Campylobacter jejuni*-colonizing poultry feed which is useful for treating or preventing the colonization of *Campylobacter jejuni* in poultry. The feed has as an active ingredient an effective amount of at least one cecal-colonizing strain of bacteria.

The present invention is further directed to a composition for use as a dietary supplement to treat or prevent the colonization of *Campylobacter jejuni* in poultry. The composition comprises an effective anti-Campylobacter producing amount of at least one cecal-colonizing strain of bacteria. The strain produces anti-Campylobacter metabolites. The composition is administered in a carrier suitable for administration to an animal.

The present invention is further directed to a process for inhibiting the colonization of *Campylobacter jejuni* in animals comprising dispensing an effective amount of at least one cecal-colonizing strain of bacteria, which produces anti-Campylobacter metabolites.

Further objects, features and advantages of the invention will be apparent from the following detailed description when taken in conjunction with the accompany drawing.

DETAILED DESCRIPTION OF THE INVENTION

The present invention is directed to biologically pure cultures of novel strains of bacteria which are capable of inhibiting or reducing the colonization of *C. jejuni* in animals. Although the present invention has application for all animals including poultry, birds, swine, horses, cattle and humans, the present invention is specifically directed to poultry and animals which have a cecum, i.e., a blind pouch in which the large intestine begins and into which the ileum opens from one side.

Microorganism Strains

The present invention is specifically directed to the following gram-negative microorganism strains, all of which have been deposited with the American Type Culture Collection (ATCC), 12301 Parklawn Drive, Rockville, Md., and have received the following accession numbers:

| Bacterial Strain | ATCC Number | Date of Deposit |
|---|---|---|
| *Klebsiella pneumoniae* strain 23 | 55234 | 9/18/91 |
| *Citrobacter diversus* strain 22 | 55236 | 9/18/91 |
| *Escherichia coli* (013:H−) strain 25 | 55235 | 9/18/91 |

This deposit is made under the provisions of the Budapest Treaty on the International Recognition of the Deposit of Microorganisms for the Purposes of Patent Procedure and the Regulations thereunder (Budapest Treaty). This assures maintenance of a viable culture for 30 years from the date of deposit. The organism will be made available by ATCC under the terms of the Budapest Treaty, and subject to an agreement between applicants and ATCC, which assures permanent and unrestricted availability of the progeny of the cultures to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto including 37 CFR §1.14 with particular reference to 886 OG 638). The assignee of the present application agrees that if the culture on deposit should die or be lost or destroyed when cultivated under suitable conditions, it will be promptly replaced on notification with a viable specimen of the same culture. Availability of the deposited strain is not to be construed as a license to practice the invention in contravention of the rights granted under the authority of any government in accordance with its patent laws.

Of primary importance to the present invention is the fact that the microorganisms listed above grow in mucin as a sole substrate. Beery et al. (1988) determined that the cecal crypts are the sites of *C. jejuni* colonization of chicks. Campylobacters accumulate in very large numbers in the mucus-filled sites, apparently due to their chemoattraction to mucin (Hugdahl, et al., 1988), where they thrive in mucin.

Further, the microorganism strains produce metabolites antagonistic to *C. jejuni*. For purposes of the present invention, the term "metabolites" identifies the products of bacterial, i.e., microorganism, metabolism. Because they also occupy the same niche (cecum) in poultry, the strains effectively reduce colonization of most chicks by *C. jejuni*.

Biochemical profiles for the three microorganisms are listed below in Table 1:

TABLE 1

| | Biochemical Profiles for "Anti-Campylobacter" Bacteria[1] | | |
|---|---|---|---|
| Test | *Citrobacter diversus* Strain 22 (ATCC #55236) | *Klebsiella pneumoni* Strain 23 (ATCC #55234) | *E. coli* (013:H−) Strain 25 (ATCC #55235) |
| ONPG[2] | + | + | + |
| ADH[3] | − | − | − |
| LDC[4] | − | + | + |
| ODC[5] | + | − | − |
| CIT[6] | − | + | − |
| H2S[7] | − | − | − |
| URE[8] | − | − | − |
| TDA[9] | − | − | − |
| IND[10] | + | − | + |
| VP[11] | − | + | − |
| GLU[12] | + | + | + |
| MAN[13] | + | + | + |
| INO[14] | − | + | − |
| SOR[15] | − | + | + |
| RHA[16] | + | + | + |
| SAC[17] | − | + | − |
| MEL[18] | − | + | + |
| AMY[19] | + | + | − |

TABLE 1-continued

Biochemical Profiles for "Anti-Campylobacter" Bacteria[1]

| Test | Citrobacter diversus Strain 22 (ATCC #55236) | Klebsiella pneumoni Strain 23 (ATCC #55234) | E. coli (013:H−) Strain 25 (ATCC #55235) |
|---|---|---|---|
| ARA[20] | + | + | + |

[1] Summary of chemical and physical principles using the API 20E miniaturized diagnostic kit (Analytab Products, Plainview, N.Y.)
[2] Hydrolysis of ONPG (O-nitrophenyl-β-d-galactoside) by beta-galactosidase releases yellow orthonitrophenol from the colorless ONPG.
[3] Arginine dihydrolase transforms arginine into ornithine, ammonia and carbon dioxide. This causes a pH rise in the acid-buffered system and a change in the indicator from yellow to red.
[4] Lysine decarboxylase transforms lysine into a basic primary amine, cadaverine. This amine causes a pH rise in the acid-buffered system and a change in the indicator from yellow to red.
[5] Ornithine decarboxylase transforms ornithine into a basic primary amine, putrescine. This amine causes a pH rise in the acid-buffered system and a change in the indicator from yellow to red.
[6] Citrate is the sole carbon source. Citrate utilization results in a pH rise and a change in the indicator from green to blue.
[7] Hydrogen sulfide is produced from thiosulfate. The hydrogen sulfide reacts with iron salts to produce a black precipitate.
[8] Urease releases ammonia from urea; ammonia causes the pH to rise and changes the indicator from yellow to red.
[9] Tryptophane deaminase forms idolepyruvic acid from tryptophane. Indolepyruvic acid produces a brownish-red color in the presence of ferric chloride.
[10] Metabolism of tryptophane results in the formation of indole. Kovacs' reagent forms a colored complex (pink to red) with indole.
[11] Acetoin, an intermediary glucose metabolite, is produced from sodium pyruvate and indicated by the formation of a colored complex. Conventional VP tests may take up to 4 days, but by using sodium pyruvate, API has shortened the required test time. Creatine intensifies the color when tests are positive.
[12] Utilization of the carbohydrate results in acid formation and a consequent pH drop. The indicator changes from blue to yellow (Glucose).
[13] Utilization of the carbohydrate results in acid formation and a consequent pH drop. The indicator changes from blue to yellow (Mannitol).
[14] Utilization of the carbohydrate results in acid formation and a consequent pH drop. The indicator changes from blue to yellow (Inositol).
[15] Utilization of the carbohydrate results in acid formation and a consequent pH drop. The indicator changes from blue to yellow (Sorbitol).
[16] Utilization of the carbohydrate results in acid formation and a consequent pH drop. The indicator changes from blue to yellow (Rhamnose).
[17] Utilization of the carbohydrate results in acid formation and a consequent pH drop. The indicator changes from blue to yellow (Sucrose).
[18] Utilization of the carbohydrate results in acid formation and a consequent pH drop. The indicator changes from blue to yellow (Melibrose).
[19] Utilization of the carbohydrate results in acid formation and a consequent pH drop. The indicator changes from blue to yellow (Amygdalin).
[20] Utilization of the carbohydrate results in acid formation and a consequent pH drop. The indicator changes from blue to yellow ((L+) Arabinose).

*C. diversus* (ATCC No. 55236) is the only strain among the above-referenced strains that is motile.

The dominant cecal microorganism in chicks treated with the 3-strain mixture appears to be *E. coli* 013:H−(ATCC No. 55235).

Selection

The cecal-colonizing microorganisms were isolated from *Campylobacter jejuni*-free laying hens and were screened for their ability to produce anti-Campylobacter metabolites. Originally, nine isolates (listed in Table 2, Infra.) possessing this characteristic were obtained. The isolates were recovered from adult chickens that did not carry *C. jejuni* in their ceca, but were constantly exposed to the organism through contact with other *C. jejuni*-colonized chickens. The methods of isolation are described elsewhere in the experimental procedures.

Preparation of Anti-Campylobacter Composition

The anti-Campylobacter composition of the present invention can be prepared by mixing the active "microorganism strain" ingredient with an inert ingredient, such as a carrier. The carrier can comprise feed stuffs, extender materials and the like. The term "inert ingredient" is intended to describe a material which does not function as an active ingredient and which may be stably ingested by animals. In this manner, the active ingredient can be orally administered as a component of the feed.

Prior to administration, the active component is first blended with the feed ingredient or carrier to become a feed additive supplement. Carriers are generally solids that are inert with respect to the active ingredient and which may be safely ingested by the animals to be treated. The nutrient carrier is used as poultry feeds and, for the purpose of this invention, as carriers for the bacterial strains of the present invention may vary depending upon the specific needs of the poultry being fed. However, for the most part, the feeds can contain sources of protein, i.e, fishmeal, corn, peanut products, etc., and sources of carbohydrates, i.e., meals, sugars, grains, etc. Additionally, minerals and vitamins can be added as required. Typical of carriers for commercial poultry feeds include ground cereal grains, grain by-products, plant protein concentrates, fermentation by-products, etc. Carriers of the anti-Campylobacter can also include water, buffers, peptone water, or any liquid medium that is not detrimental to the bacteria and the chicks.

The bacteria may be dried in the presence of a growth medium, nonfat dry milk or a protective substance and fed to chicks in dry, powder form. The bacteria may also be suspended in liquid such as water and administered to chicks or eggs at the time the chicks begin to pip.

Additionally, the active ingredient can be administered to the poultry by means of an aerosol spray. By this, it is meant that the active strain is placed in a liquid extender, such as water, and simply sprayed on the outer surface of the animal or the egg. In this manner, a sufficient amount of the required strain will be taken up into the animal for therapeutic purposes.

The bacteria may also be administered into the air space of eggs before chicks hatch, or into chicks by cloacal introduction.

CONCENTRATION OF INGREDIENTS

The actual concentration of the active ingredient can, of course, be adjusted to the individual needs and may vary over a wide range. The concentration must provide a sufficient amount of active ingredient to effect the desired control and/or elimination of *C. jejuni* in the animal while preventing any undesirable side effects.

In a feed pre-mix or supplement, a sufficient daily amount of active ingredient to provide anti-Campylobacter activity is at least approximately 100 colony forming units (CFU) of protective bacteria per animal, preferably at least about $10^5$ CFU, and most preferably about $10^8$–$10^9$ CFU. A CFU is defined as a quantity of microorganisms sufficient to develop into a culture colony on a culture medium.

In poultry, it is important to administer the dosage to the animals soon after birth. Generally, all that is required is a one-time dosage of the ingredients within the first seven days of birth. The dosage can be orally administered, administered by aerosol or administered before birth by application to the egg in the manner described previously. In view of the young age of the animals, it is preferred to administer the anti-Campylobacter composition by aerosol in order to ensure that an effective amount will be absorbed into the animal's body.

The following examples are presented to illustrate the advantages of the present invention and to assist one of ordinary skill in making and using the same. The examples are not intended in any way to otherwise limit the scope of the disclosure or the protection granted by the patent.

EXPERIMENTS

Experiment 1

Determination of C. jejuni Negative Hens 2,320 white leghorn laying hens from one commercial flock and two research flocks were assayed for intestinal carriage of C. jejuni according to the following procedure. Cloacal swabs were obtained from one bird in each cage. Legs of the birds tested were marked with permanent marker for later identification. Swabs were placed individually in tubes with 3 ml of 0.1% sterile peptone water and transported to the laboratory on ice. Each swab was streaked onto two Campy BAP (Brucella agar [Difco Laboratories, Detroit, Mich.] plus Campylobacter selective supplements, Oxoid U.S.A., Columbia, Md.) plates. Plates were incubated microaerobically (5% $O_2$, 10% $CO_2$, 85% $N_2$) in BBL Gas Pak jars (BBL Microbiology Systems, Cockeysville, Md.) at 42° C. for 48 hours. Hens with cloacal samples that had no colonies typical of Campylobacter on Campy BAP plates were tested a second time. For the second sampling, in addition to direct plating onto Campy BAP, the swab plus remaining 0.1% peptone was placed in enrichment broth and tested for C. jejuni according to the procedure of Doyle and Roman (1982).

Feces or cecal contents are added to 100 ml of enrichment medium (comprised of brucella broth, 7% lysed horse blood, 0.3% sodium succinate, or 0.01% cysteine hydrochloride, 15 µg vancomycin/ml, 5 µg trimethoprim/ml, 20 IU polymyxin B/ml, and 50 µg cycloheximide/ml.) in a 250-ml side arm Erlenmeyer flask. The flask is evacuated three times to 20 in. Hg, and the atmosphere is replaced with 5% $O_2$, 10% $CO_2$, 85% $N_2$. The flask is shaken (100 gyrations/min) in a waterbath at 42° C. for 16 to 18 hours, and the enrichment culture is plated onto Campy BAP agar plates (comprised of brucella agar, 10% sheep blood, 10 µg vancomycin/ml, 5 µg trimethoprim/ml, 2.5 IU polymyxin B/ml, 2 µg amphotericin B/ml, and 15 µg cephalothin/ml). Campy BAP plates are incubated under 5% $O_2$, 10% $CO_2$, 85% $N_2$ at 42° C. for 48 hours. Colonies typical of Campylobacter jejuni, i.e., gray to tan, non-hemolytic, small (1–2 mm diameter) and mucoid, are selected and confirmed as C. jejuni by appropriate microscopic and biochemical tests.

Hens negative for C. jejuni by enrichment were sacrificed and ceca were removed for isolation of mucus-dwelling bacteria.

Of the 2,320 laying hens from three flocks assayed for intestinal carriage of C. jejuni, only 8 (0.3%) were not colonized by the organism.

Experiment 2

Isolation of the Mucus-Dwelling Bacteria

Hens with cloacal samples negative for C. jejuni were asphyxiated by exposure to carbon dioxide. The lower intestine was surgically exposed and the ceca were removed. Cecal contents were assayed for C. jejuni according to the enrichment procedure described in Experiment 1.

Each cecum was slit lengthwise with a sterile scalpel, opened and rinsed three times with sterile 0.01M phosphate buffered saline (PBS), pH 7.2, to remove cecal contents. Any residual cecal contents were removed by gently scraping a sterile microscope slide across the cecal epithelium. The mucus layer was then removed by applying increased pressure on the slide across the epithelial surface. This mucus preparation was diluted 1:10 (wt/vol) in 0.01M PBS and mixed for 2 min. in a Vortex mixer. Portions (0.1 ml) of serial (1:10) dilutions were spread plated onto four plates each of liver veal agar (LVA; Difco), tryptic soy agar (TSA; Difco), and TSA with 5% defibrinated sheep blood for each dilution. One plate of each dilution and each medium was incubated for 48 hours at 42° C. microaerobically (5% $O_2$, 10% $CO_2$, 85% $N_2$, at 42° C. aerobically, at 37° C. microaerobically, and 37° C. aerobically. Colonies appearing morphologically different were picked and restreaked onto TSA for purity.

Screening Cecal Isolates for Ability to Use Mucin as Sole Substrate for Growth. Growth of each cecal isolate that was capable of producing anti-Campylobacter metabolites was determined in different concentrations (0.01%, 0.1%, 1.0% wt/vol) of porcine gastric mucin (Sigma Chemical Company, St. Louis, Miss.) in 0.01M PBS, pH 7.0. Mucin preparations were solubilized to the appropriate concentrations in 0.01M PBS, pH 7.0, heated to 70° C., and were tested for growth of indigenous bacteria by plating onto TSA (37° C., 48 hours). No contaminating bacteria grew in mucin preparations used for these studies. Each mucin preparation was inoculated with ca. $6 \times 10^2$ CFU cecal isolate/ml and incubated at 37° C. A 0.5-ml sample was taken at 0, 4, 8, 20, 35, and 48 hours postinoculation, diluted in 0.01M PBS, pH 7.0, and plated on TSA (37° C., 48 hours) for enumeration of bacteria.

Figure 1:
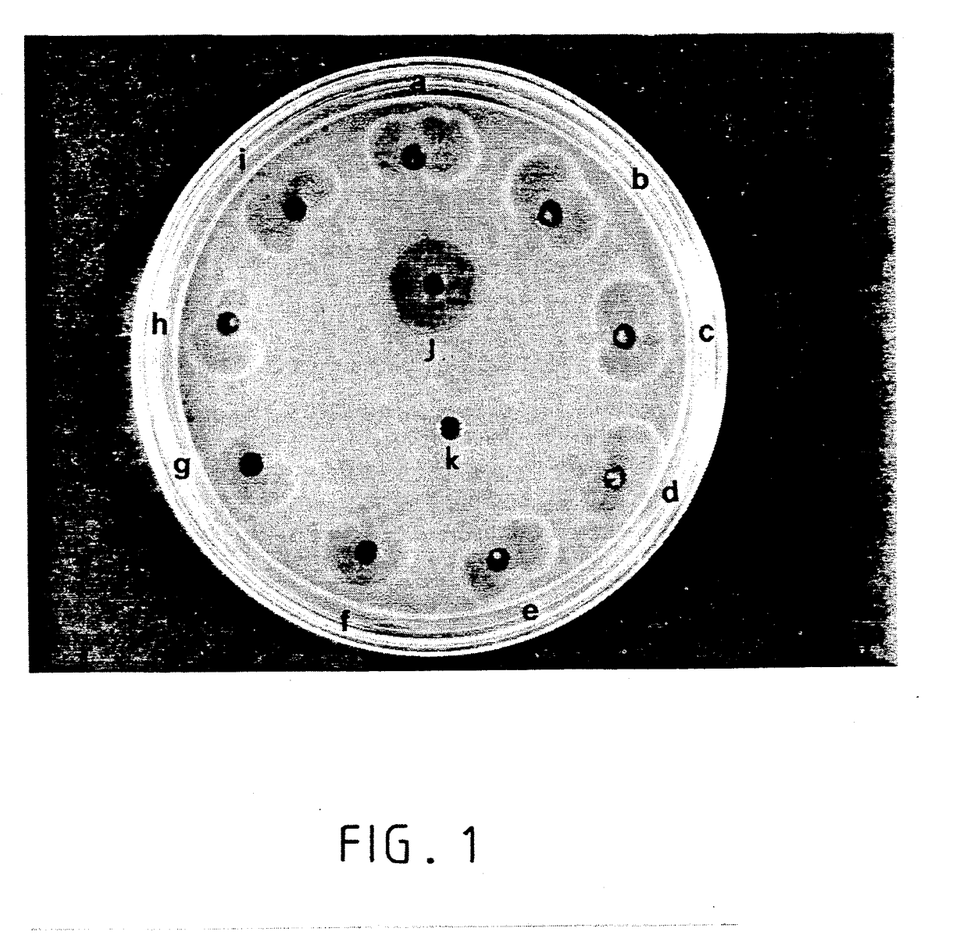
FIG. 1 is a photograph of culture extracts of cecal isolates in brucella agar held microaerobically (5% $O_2$, 10% $CO_2$, 85% $N_2$ at 42° C. for 8 hours). Wells a–i contain 35 microliters (ul) of culture extract of: (a) CDC Group IIK 17, (b) CDC Group IIK 18, (c) *Pasteurella multocida* 19, (d) *Micrococcus roseus* 20, (e) *Klebsiella pneumoniae* 21, (f) *Citrobacter diversus* 22, (g) *Klebsiella pneumoniae* 23, (h) *Proteus mirabilis* 24, and (i) *Escherichia coli* 25. Well j is a positive control with 35 ul of 0.3 N acetic acid, and well k is a negative control with 35 ul of extract of TSA with no bacterial growth.

Reference is made to FIG. 1 and Table 2, which follows, for an illustration and description of the results.

TABLE 2

Isolation medium and ability of cecal isolates to grow on mucin (as a sole substrate) in 0.01M PBS at 37° C. for 48 hours.

| Cecal Isolate | Isolation medium[a] | Growth or Death[b] of Organism ($\log_{10}$ CFU/ml) in: | | |
| --- | --- | --- | --- | --- |
| | | 0.01% Mucin | 0.1% Mucin | 1% Mucin |
| CDC Group II K 17 | TSA plus 5% blood | −0.96 | −1.43 | −1.26 |
| CDC Group II K 18 | TSA plus 5% blood | −1.20 | −1.07 | −1.15 |
| Pasteurella multicida 19 | TSA | +0.10[c] | +0.15[c] | +0.03[c] |
| Micrococcus roseus 20 | TSA | −2.24 | −2.14 | +0.03 |
| Klebsiella pneumoniae 21 | TSA | +4.49 | +4.64 | +4.74 |
| Citrobacter diversus 22 | TSA | +5.03 | +5.65 | +5.83 |
| Klebsiella pneumoniae 23 | TSA | +4.74[c] | +4.90 | +4.76[c] |
| Proteus mirabillis 24 | LVA | +0.03[c] | +0.10[c] | 0.00 |
| Escherichia coli 25 | TSA | +4.30 | +5.14 | +4.81 |

[a]Isolates recovered from plates that were incubated aerobically at 37° C.
[b]−, death; +, growth
[c]Cell count was at 35 hours when the largest population was observed; cell count decreased at 48 hours.

Nine bacteria capable of producing metabolites inhibitory to C. jejuni were isolated from the mucus scrapings of ceca from these eight hens. All isolates were recovered from plates incubated aerobically at 37° C. Strains No. 17 and 18 were isolated from TSA with 5% sheep blood, strain 24 from LVA, and the remaining strains from TSA. Microaerobic conditions did not produce morphologically unique colonies from those that developed under aerobic conditions. Filter-sterilized extracts of cultures of the nine cecal isolates produced approximately equal zones of inhibition (FIG. 1). The cecal isolates were identified as: CDC Group IIK (2 strains),

*Pasteurella multocida, Micrococcus roseus, Klebsiella pneumoniae* (2 strains), *Citrobacter diversus. Proteus mirabilis,* and *Escherichia coli* 013:H−.

Four of the nine isolates grew prolifically (4 $\log_{10}$ CFU/ml increase within 48 hours at 37° C.) in mucin at all three concentrations (0.01, 0.1, and 1%), hence they were capable of utilizing mucin as a sole substrate for growth. These included: *K. pneumoniae* (2 strains), *C. diversus,* and *E. coli.* Death or inconsequential growth (0.15 $\log_{10}$ CFU/ml increase) occurred within 48 hours for the other five isolates in all three concentrations of mucin. In addition, motility studies revealed that only two isolates, i.e., *C. diversus* and *P. mirabilis,* were motile.

Experiment 3

Screening Cecal Isolates for Anti-Campylobacter Metabolite Production

Isolates were screened for expression of inhibitory metabolites to *C. jejuni* by two methods. One method involved spot-inoculating four isolates per plate onto semi-solid brucella agar (0.75% agar), incubating at 37° C. for 16-18 hours, exposing bacterial growth to chloroform for 2 hours, and layering the surface of the agar with 10 ml of 0.4% brucella agar with ca. $5 \times 10^8$ *C. jejuni* 74 C/ml. Plates were incubated microaerobically at 42° C. for 16-48 hours and observed for zones of inhibition to *C. jejuni* growth.

Cecal isolates with zones of inhibition were then assayed by a second procedure. This involved spread inoculating, with a PBS moistened swab, 0.2 ml of ca. $10^8$ cells of each cecal isolate individually onto TSA. Cultures were grown overnight at 37° C., then frozen at −20° C. for 24 hours followed by thawing for 2 hours at 37° C. The liquefied culture medium was centrifuged for 20 min at 1000 ×g and the supernatant was filtered through a 0.45-um Gelman Acrodisc filter (Gelman Sciences, Ann Arbor, Mich.). The pH of the supernatant was adjusted to 7.0 with 1 N NaOH or 1 N HCl. *C. jejuni* 74 C was grown microaerobically at 42° C. for 48 hours on brucella agar with 5% defibrinated sheep blood, washed three times in PBS and adjusted with PBS to an optical density (500 nm) ($OD_{500nm}$) =6 (ca. $1 \times 10^{10}$/ml). One ml of culture was added to 100 ml of semi-solid brucella agar (0.5% agar) tempered to 42° C. The medium was gently swirled to distribute the campylobacters and 30 ml was dispensed, under a static hood, into $15 \times 100$ mm disposable petri dishes. The medium was held at room temperature for 1 hour, then nine perimeter and two center plugs were out from the medium with a sterile 4-mm cork borer. Agar plugs were removed from each plate with an aspirator equipped with a 200-ul pipet tip inserted into the end of the tubing. Supernatant (35 ul/well) of cultures of cecal isolates was added immediately to the wells. Acetic acid (0.3N) was used as a positive control and supernatant of uninoculated TSA treated in the same manner as the inoculated TSA plates was the negative control. Plates were placed in BBL Gas Pak jars and cultures were incubated in an atmosphere of 5% $O_2$, 10% $CO_2$, 85% $N_2$ at 42° C. for 6-8 h, then examined for zones of inhibition.

Twelve trials were conducted to evaluate the protective ability of mucus-dwelling, cecal bacteria in preventing or reducing intestinal colonization of chicks by *C. jejuni.* A minimum of 25% of chicks treated only with *C. jejuni* (positive control groups) must have been colonized by campylobacters for a trial to be considered significant. Four trials were excluded from the study because they did not meet this criterion.

The initial five trials evaluated the ability of all nine cecal isolates in combination at approximately equal concentrations (total inocula of 3.3 $\times 10^8$–3.5$\times 10^9$ CFU/chick) to reduce colonization by one strain of *C. jejuni* (either 74 C or A74 C) inoculated at levels of $6.7 \times 10^8$–$1.8 \times 10^{10}$ CFU/chick. *C. jejuni* was competitively excluded from 41 to 85% (avg. 64%) of chicks that received the nine-strain cecal bacteria.

The average number of *C. jejuni* in ceca of chicks inoculated with *C. jejuni* ranged from 1.3 to 4.9 $\log_{10}$ CFU/g for the five trials, whereas in chicks inoculated with the nine-strain cecal isolates and then *C. jejuni* the Campylobacter counts of colonized chicks ranged from 1.1 to 1.5 $\log_{10}$ CFU/g. The nine-strain cecal isolates consistently reduced the number of *C. jejuni* colonizing chick ceca for those chicks colonized by the organism, and the average number of *C. jejuni* present in ceca was relatively low, i.e., ≦1.5 $\log_{10}$ CFU/g. The greatest difference between the two treatments occurred in Trial No. 1 in which average populations of 4.9 $\log_{10}$ *C. jejuni*/g were detected in chicks administered *C jejuni* only versus average populations of 1.2 $\log_{10}$ *C. jejuni*/g were detected in chicks receiving the protective cecal bacteria followed by *C. jejuni.* Differences between treatments for the other four trials were less dramatic, i.e., only 0.2 to 0.4 $\log_{10}$ *C. jejuni*/g.

The next approach was to determine if the number of strains in the nine-strain mixture of cecal bacteria could be reduced and still provide a protective effect. Hence, three strains were selected for further study based principally on their ability to utilize mucin as a sole substrate for prolific growth. These included *C. diversus* 22, *K. pneumoniae* 23, and *E. coli* 25. Although two strains of *K. pneumoniae* (21 and 23) grew prolifically in mucin, only one was selected for use in order to keep the number of strains to a minimum. *K. pneumoniae* strain 23 was selected on the basis of its ability to produce a slightly larger zone of inhibition toward *C. jejuni* than *K. pneumoniae* strain 21. In addition, the experimental approach was modified slightly for the chick challenge studies. These changes included growing cecal isolates on TSA plates instead of in TSB, using five strains of *C. jejuni* instead of one to challenge chicks (except Trial No. 6), and growing each strain of *C. jejuni* on brucella blood agar plates instead of in brucella broth. These changes were made to increase the chances and levels of *C. jejuni* colonization and to evaluate the ability of the cecal isolates to inhibit a variety of strains of *C. jejuni* instead of only one. The number of bacteria in the 3-strain mixture of cecal isolates and in the 5-strain mixture of *C. jejuni* were approximately the same as those used in the previous studies with the 9-strain mixture of cecal isolates. Four trials were performed with the 3-strain mixture of cecal isolates.

Identification of Cecal Isolates. All isolates capable of producing anti-Campylobacter metabolites and utilizing mucin as a sole substrate were identified using the API 20 E miniaturized diagnostic kit (Analytab Products, Plainview, N.Y.) for gram-negative bacteria (see Table 1 supra.) or using the schemata described by MacFaddin (21) and Howard (14) for gram-positive bacteria. One isolate, strain 25, was verified as *Escherichia coli* by the Wisconsin State Laboratory of Hygiene and later serotyped by H. Lior, Laboratory Centre for Disease Control, Health and Welfare Canada, Ottawa.

Evaluation of Protective Effect of Cecal Isolates in Colonization of Chicks. For Trials No. 1-5, each strain of cecal isolate was grown in 50 ml tryptic soy broth (TSB; Difco) at 37° C. for 16-18 hours. Cells were sedimented by centrifugation (1000 ×g, 20 min) then washed three times in 0.01M PBS, pH 7.2, by alternate centrifugation and resuspension in PBS. Cells were adjusted in PBS to an $OD_{500nm}=2.0$ (ca. $10^9$ CFU/ml) For Trials No. 6-12, each strain of cecal isolate was grown as a lawn on TSA plates (2-4 plates/isolate) at 37° C. for 20 hours. Cells were harvested in 3 ml PBS per plate by rubbing the agar surface with a sterile curved glass rod. Cells were washed and adjusted to ca. $10^9$ CFU/ml according to the procedures described above. Cell counts of each suspension were determined by plating appropriate dilutions onto TSA and incubating plates at 37° C. for 18-24 hours. Cells (ca. $10^9$ CFU/ml) of appropriate strains were combined, then enumerated according to the procedure described above. C. jejuni, strain 74 C, was grown on brucella agar with 5% sheep blood at 42° C. for 48 hours in Gas Pak jars with a micro-aerobic atmosphere (5% $O_2$, 10% $CO_2$, 85% $N_2$). Cells were harvested, sedimented and washed according to the procedure described above, then resuspended in PBS to an $OD_{500nm}=5.6$ (ca. $5\times10^9$ CFU/ml). Campylobacter numbers were determined culturally on brucella agar with 5% sheep blood (42° C., 48 hours, microaerobic atmosphere).

Approximately 120 one-day-old White Leghorn cockerel chicks were divided equally into three groups. Each group received orally one of the following treatments: (a) a mixture of cecal ($10^8$-$10^9$ CFU / chick) isolates followed 7 days later by C. jejuni ($10^8$-$10^9$ CFU /chick), (b) PBS followed 7 days later by C. jejuni ($10^8$-$10^9$ CFU / chick), or (c) a mixture of cecal isolates ($10^8$-$10^9$ CFU/ chick) followed 7 days later by PBS. Each chick received 0.5 ml of bacterial suspension or PBS via a 20 gauge, ball-tipped cannula. Chicks were housed in individual cages (24.0 cm length×17.5 cm width×17.5 cm height; constructed of stainless steel wire) to prevent cross contamination, at the University of Wisconsin Biotron, which provides controlled experimental environments. Temperature, beginning at 37.8° C., was reduced 0.6° C. each day. Relative humidity remained constant (50%) for the duration of each experiment and lights were cycled 12 hours on and 12 hours off.

At 21±2 days postinoculation, chicks were sacrificed by $CO_2$ asphyxiation, aseptically surgically exposed, and ceca were removed. For control chicks of Trials No. 7-12 which received only cecal isolates, one cecum was assayed to identify the dominant bacteria and the other cecum was assayed for C. jejuni. The dominant bacteria colonizing the ceca were obtained by the same procedure used to isolate mucus-dwelling bacteria, except 0.1 ml portions of serial 1:10 dilutions were plated only onto TSA. Plates were incubated aerobically at 37° C. for 18-24 hours. All colonies were counted according to morphology and recorded. Ten colonies of the predominant flora and two colonies of each additional morphological type were picked and identified by API 20E diagnostic kit or MacFaddin (1980) and Howard (1987) schemata. E. coli isolates were assayed by slide agglutination for reaction with 013 antiserum (E. coli Reference Center, Pennsylvania State, University Park, Pa.).

Both ceca of chicks receiving the other two treatments were assayed for C. jejuni. Ceca were homogenized in PBS (1:10, wt/vol) for 2 min with a Brinkmann Homogenizer (Model PT 10/35, Brinkmann Instruments Inc., Westbury, N.Y.) and serially (1:10) diluted in PBS. Ten 0.1-ml portions of the homogenate were directly surface plated onto Campy BAP agar, whereas each 1:10 dilution was plated in duplicate. Campy BAP plates were incubated at 42° C. for 48 hours in a microaerobic atmosphere, and colonies typical of C. jejuni were counted. Randomly selected colonies were confirmed as C. jejuni according to the methods described in Doyle and Roman (1982), which is described supra. Percent protection was calculated using the following equation:

% Protection $=[1-A/B]\times100$ where A=the % chicks colonized by C. jejuni when inoculated first with cecal isolates, followed with inoculation with C. jejuni; and B=% chicks colonized by C. jejuni when inoculated with C. jejuni.

Reference is made to Table 3 as follows for a description of the results:

TABLE 3

Effect of cloacal isolates on cecal bacterial colonization of chicks by C. jejuni.

| Cecal Bacteria Isolates Inoculum (CFU/chick) | C. jejuni Inoculum (CFU/chick) | Strains of C. jejuni | Colonization of chicks by C. jejuni | | % Chicks Protected | $\log_{10}$ CFU C. jejuni per Gram of Ceca of Colonized Chicks[a] | | Dominant Cecal Bacteria |
|---|---|---|---|---|---|---|---|---|
| | | | Chicks inoculated with C. jejuni only | Chicks Inoculated with Cecal Isolates, then C. jejuni | | Chicks inoculated with C. jejuni | Chicks Inoculated with Cecal Isolates, then C. jejuni | |
| [No. chicks with C. jejuni/No. chicks tested (%)] | | | | | | | | |
| 9-Strain Mixture[b] | | | | | | | | |
| Trial 1  3.4 × $10^9$ | 6.8 × $10^8$ | 74C | 32/34 (94.1) | 4/28 (14.3) | 84.8 | 4.9 ± 1.9 | 1.2 ± 0.6 | ND[f] |
| 2  3.5 × $10^9$ | 2.2 × $10^9$ | 74C | 19/32 (59.4) | 13/37 (35.1) | 40.8 | 1.7 ± 0.8 | 1.5 ± 0.8 | ND[f] |
| 3  3.3 × $10^9$ | 1.4 × $10^9$ | 74C | 12/34 (35.3) | 5/56 (13.9) | 60.6 | 1.3 ± 0.6 | 1.1 ± 0.4 | ND[f] |
| 4  3.0 × $10^9$ | 5.1 × $10^9$ | A74C | 20/36 (55.6) | 7/34 (20.6) | 62.9 | 1.8 ± 1.0 | 1.5 ± 1.1 | ND[f] |
| 5  3.3 × $10^8$ | 1.8 × $10^8$ | A74C | 20/40 (50.0) | 6/38 (15.8) | 68.4 | 1.7 ± 1.8 | 1.3 ± 0.9 | ND[f] |
| 3-Strain Mixture[c] | | | | | | | | |
| Trial 6  1.8 × $10^{10}$ | 2.1 × $10^8$ | A74C | 11/44 (25.0) | 2/38 (5.3) | 78.8 | 1.6 ± 1.2 | 1.1 ± 0.5 | ND[f] |
| 7  1.3 × $10^9$ | 8.4 × $10^9$ | 5-strains[e] | 21/45 (46.7) | 2/40 (5.0) | 89.3 | 2.0 ± 1.4 | 1.1 ± 0.6 | E. coli 013:H$^-$ |
| 8  7.5 × $10^8$ | 4.5 × $10^8$ | 5-strains[e] | 13/36 (36.1) | 0/46 (0.0) | 100.0 | 1.5 ± 0.6 | 1.0 ± 0.0 | E. coli 013:H$^-$ |
| 9  8.2 × $10^8$ | 1.7 × $10^9$ | 5-strains[e] | 35/40 (87.5) | 21/42 (50.0) | 42.9 | 3.7 ± 1.8 | 2.4 ± 1.7 | E. coli 013:H$^-$ |
| 1-Strain Mixture[d] | | | | | | | | |
| Trial 10  2.2 × $10^9$ | 2.9 × $10^8$ | 5-strains[e] | 19/40 (47.5) | 11/45 (24.4) | 48.6 | 2.8 ± 2.2 | 2.2 ± 2.1 | E. coli 013:H$^-$ |
| 11  1.3 × $10^9$ | 1.5 × $10^9$ | 5-strains[e] | 13/39 (33.3) | 8/44 (18.2) | 45.3 | 2.4 ± 2.1 | 2.0 ± 2.1 | E. coli 013:H$^-$ |

TABLE 3-continued

Effect of cloacal isolates on cecal bacterial colonization of chicks by *C. jejuni*.

| Cecal Bacteria Isolates Inoculum (CFU/chick) | *C. jejuni* Inoculum (CFU/chick) | Strains of *C. jejuni* | Colonization of chicks by *C. jejuni* | | % Chicks Protected | $\log_{10}$ CFU *C. jejuni* per Gram of Ceca of Colonized Chicks[a] | | Dominant Cecal Bacteria |
|---|---|---|---|---|---|---|---|---|
| | | | Chicks inoculated with *C. jejuni* only | Chicks Inoculated with Cecal Isolates, then *C. jejuni* | | Chicks inoculated with *C. jejuni* | Chicks Inoculated with Cecal Isolates, then *C. jejuni* | |
| 12  $1.3 \times 10^9$ | $2.0 \times 10^{10}$ | 5-strains[e] | 31/43 (72.1) | 8/40 (20.0) | 72.3 | 3.4 ± 2.0 | 2.0 ± 2.0 | *E. coli* 013:H⁻ |

[a] Values reported are the geometric mean ± standard deviation; all *C. jejuni* counts of <10 CFU/g were given the value of 1 for calculation purposes.
[b] 9 strains = CDC Group IIK strains 17 and 18, *Pasteurella multocida* strain 19, *Micrococcus roseus* strain 20, *Klebsiella pneumoniae* strains 21 and 23. *Citrobacter diversus* strain 22, *Proteus mirabilis* strain 24, and *Escherichia coli* strain 25, approximately equal numbers of each strain were used.
[c] 3 strains = *Citrobacter diversus* 22, *Klebsiella pneumoniae* 23, *Escherichia coli* 25, approximately equal numbers of each strain were used.
[d] 1 strain = *Escherichia coli* 25.
[e] 5 strains *C. jejuni* = 74C, A74C, OCH-1, CF 108, CF 115; approximately equal numbers of each strain were used.
[f] ND, not determined.

The results indicate that the cecal isolates were very effective in reducing colonization by *C. jejuni* in three of four trials. Only 2 of 38 (5.3%) chicks in Trial No. 6, 2 of 40 (5%) chicks in Trial No. 7, and 0 of 46 (0%) chicks in Trial No. 8 receiving the cecal isolates before challenge with Campylobacter were colonized by *C. jejuni*. In contrast, 21 of 42 chicks (50%) were colonized by *C. jejuni* in Trial No. 9.

The dominant bacterial flora of ceca of chicks inoculated only with cecal isolates (no *C. jejuni*) was determined by assaying a cecum of each of 20 chicks per study. The dominant organism in 57 of 60 (95%) chicks was *E. coli* 013:H⁻, which was present at an average level of $5.0 \times 10^7$ CFU/g. This organism was present among 50-100% of the 10 colonies recovered and identified from each chick.

Since *E. coli* 013:H⁻, which was one of the three cecal isolates used to inoculate the chicks, was among the dominant cecal bacterial flora, additional studies were done to determine if this organism alone could competitively exclude *C. jejuni* from cecal colonization of chicks. *E. coli* strain 25 and *C. jejuni* (5-strain mixture) were grown on agar media as was done for studies with the 3-strain mixture. Chicks were each administered $1.3 \times 10^9$–$2.2 \times 10^9$ *E. coli* strain 25 and/or $1.5 \times 10^9$–$2.9 \times 10^9$ *C. jejuni*. Although *E. coli* strain 25 provided chicks substantial protection from colonization by *C. jejuni*, i.e., 49-72% of chicks were protected (Table 2), the average level of protection was less than that observed with the 3-strain mixture. Chicks inoculated with *E. coli* strain 25 that were colonized by *C. jejuni* had lower levels (ranging from 0.4-1.4 $\log_{10}$ CFU/g) of campylobacters than chicks inoculated with only *C. jejuni*. However, the levels of *C. jejuni* in ceca of *E. coli* strain 25-treated birds were about 1 $\log_{10}$ CFU/g higher than in *C. jejuni* colonized chicks treated with the 3-strain or 9-strain mixtures of cecal isolates. The maximum number of *C. jejuni* in ceca of chicks receiving *C. jejuni* only was $1.2 \times 10^8$ CFU/g, whereas a cecum of one chick receiving the 9-strain mixture before receiving *C. jejuni* had a maximum number of $8.1 \times 10^5$ *C. jejuni*/g.

Cross-contamination of chicks within experimental housing was minimal, being detected only in one trial. *C. jejuni* was detected in 2 of 336 (0.6%) chicks receiving only cecal isolates but no *C. jejuni*. *C. jejuni*-contaminated chicks were detected only in Trial No. 5.

It is understood that the invention is not confined to the particular construction and arrangement herein illustrated and described, but embraces such modified forms thereof as come within the scope of the claims following the Reference to Citations.

REFERENCE TO CITATIONS

1. Baker, R. C., M. D. C. Paredes, and R. A. Qureshi 1987. "Prevalence of *Campylobacter jejuni* in eggs and poultry meat in New York State." *Poultry Sci.* 66: 1766-1770.

2. Beery, J. T., M. B. Hugdahl, and M. P. Doyle. 1988. "Colonization of gastrointestinal tracts of chicks by *Campylobacter jejuni*." *Appl. Environ. Microbiol.* 54: 2365-2370.

3. Blaser, D. N. Taylor, and R. A. Feldman. 1983. "Epidemiology of *Campylobacter jejuni* infections." *Epidemiol. Rev.* 5: 157-176.

4. Brouwer, R., M. J. Mertens, T. H. Siem, and J. Katachaki. 1979. "An explosive outbreak of Campylobacter enteritis in soliders." *Antonie van Luewenhook J. Microbiol.* 45: 517-519.

5. Butzler, J. P. and M. B. Skirrow. 1979. "Campylobacter enteritis." *Clin. Gastroenterol.* 8: 737-765.

6. Deming, M. S., R. V. Tauxe, P. A. Blake, S. E. Dixon, B. S. Fowler, T. S. Jones, E. A. Lockamy, C. M. Patton, and R. O. Sikes. 1987. "Campylobacter enteritis at a university: transmission from eating chicken and from cats." *Am. J. Epidemiol.* 126: 526-534.

7. Doyle, M. P. and D. J. Roman. 1982. "Recovery of *Campylobacter jejuni* and *Campylobacter coli* from foods by selective enrichment." *Appl. Environ. Microbiol.* 43: 1343-1353.

8. Grant, I. H., N. J. Richardson, and V. D. Bokkenheuser. 1980. "Broiler chickens as a potential source of Campylobacter infections in humans." *J. Clin. Microbiol.* 500-510.

9. Harris, N. V., D. Thompson, D. C. Martin, and C. M. Nolan. 1986. "A survey of Campylobacter and other bacterial contaminants of pre-market chicken and retail poultry and meats, King County, Washington." *Am. J. Publ. Health* 76: 401-406.

10. Harris, N. V., N. S. Weiss, and C. M. Nolan. 1986. "The role of poultry and meats in the etiology of *Campylobacter jejuni/coli* enteritis." *Am. J. Publ Health* 76: 407-411.

11. Hood, A. M., A. D. Pearson, and M. Shahamat. 1988. "The extent of surface contamination of retail chickens with *Campylobacter jejuni* serogroups." *Epidemiol. Infect.* 100: 17-25.

12. Hopkins, R. S. and A. S. Scott. 1983. "Handling raw chickens as a source for sporadic *Campylobacter jejuni* infections." *J. Infect. Dis.* 148: 770.

13. Hopkins, R. S., R. Olmsted, and G. R. Istre. 1984. "Endemic *Campylobacter jejuni* infection in Colorado: identified risk factors." *Am. J. Publ. Health* 74:249-250.

14. Howard, B. J. (ed.). 1987. *Clinical and Pathogenic Microbiology*. C. V. Mosby, St. Louis, Mo., pp. 299-301, 304-307, 440.

15. Hugdahl, M. B., J. T. Beery, and M. P. Doyle. 1988. "Chemotactic behavior of Campylobacter jejuni." *Infect. Immun.* 51: 536-546.

16. Humphrey, T. J. D. G. Lanning, and G. C. Mead. 1989 "Inhibition of *Campylobacter jejuni* in vitro by broiler chicken cecal contents." *Vet. Rec.* 125: 272-273.

17. Istre, G. R., M. J. Blaser, P. Shillam, and R. S. Hopkins. 1984. "Campylobacter enteritis associated with undercooked barbecued chicken." *Am. J. Publ. Health* 74: 1265-1267.

18. Kaino, K., H. Hayashidani, K. Kaneko, and M. Ogawa. 1988. "Intestinal colonization of *Campylobacter jejuni* in chickens." *Jon. J. Vet. Sci.* 50: 489-494.

19. Kinde, H., C. A. Genigeorgis, and M. Pappainou. 1983. "Prevalence of *Campylobacter jejuni* in chicken wings." *Appl. Environ. Microbiol.* 45: 1116-1118.

20. Lee, A., J. L. O'Rourke, P. J. Barrington, and T. J. Trust. 1986. "Mucus colonization as a determinant of pathogenicity in intestinal infection by Campylobacter jejuni: a mouse cecal model." *Infect. Immun.* 51: 536-546.

21. MacFaddin, J. F. 1980. Biochemical Tests for Identification of Medical Bacteria, 2nd ed. Williams and Wilkins, Baltimore, Md., pp. 346, 360-369, 411-438.

22. Norkrans, G., and A. Svedhem. 1982. "Epidemiological aspects of *Campylobacter jejuni* enteritis." *J. Hyg.* 89: 163-170.

23. Oosterom, J., S. Notermans, H. Karman, and G. B. Engels. 1983. "Origin and prevalence of *Campylobacter jejuni* in poultry processing." *J. Food. Prot.* 46: 339-344.

24. Prescott, J. F., and C. W. Bruin-Mosch. 1981. "Carriage of *Campylobacter jejuni* in healthy and diarrhetic animals." *Am. J. Vet. Res.* 42: 164-165.

25. Rettig, P. J. 1979. "Campylobacter infections in human beings." *J. Pediatr.* 94: 855.

26. Rosenfield, J. A., G. J. Arnold, G. R. Savey, R. S. Archer, and W. H. Woods. 1985. "Serotyping of *Campylobacter jejuni* from an outbreak of enteritis implicating chicken." *J. Infect.* 11: 159-165.

27. Sanyal, S. C., K. M. N. Islam, P. K. B. Neogy, P. Speelman, and M. I. Huq. 1984. "*Campylobacter jejuni* diarrhea model in infant chickens." *Infect. Immun.* 43: 931-936.

28. Shanker, S., A. Lee, and T. C. Sorrell. 1986. "*Campylobacter jejuni* in broilers: the role of vertical transmission." *J. Hyg.* 96: 153-159.

29. Shanker, S., A. Lee, and T. C. Sorrell. 1988. "Experimental colonization of broiler chicks with *Campylobacter jejuni*." *Epidemiol. Infect.* 100: 27-34.

30. Shanker, S., A. Lee, and T. C. Sorrell. 1990. "Horizontal transmission of *Campylobacter jejuni* amongst broiler chicks: experimental studies." *Epidemiol. Infect.* 104: 101-110.

31. Soerjadi, A. S., G. H. Snoeyenbos, and O. M. Weinack. 1982. "Intestinal colonization and competitive exclusion of *Campylobacter fetus* subsp. jejuni in young chicks." *Avian Dis.* 26: 520-524.

32. Soerjadi-Liem, A. S., G. H. Snoeyenbos, and O. M. Weinack. 1984. "Comparative studies on competitive exclusion of three isolates of *Campylobacter fetus* subsp. jejuni in chickens by native gut microflora " *Avian Dis.* 28: 139-146.

33. Stern, N. J. and S. U. Kazmi. 1989. "Campylobacter." p. 71-110. In M. P. Doyle (ed.). *Foodborne bacterial pathogens*. Marcel Dekker, New York.

34. Stern, N. J. and J. S. Bailey, L. C. Blankenship, N. A. Cox, and F. McHan. 1988. "Colonization characteristics of *Campylobacter jejuni* in chick ceca." *Avian Dis.* 32: 330-334.

35. Stern, N. J., M. P. Hernandez, L. Blankenship, K. E. Deibel, S. Doores, M. P. Doyle, H. Ng, M. D. Pierson, N. J. Sofos, W. H. Sveum, and D. C. Westhoff. 1985. "Prevalence and distribution of *Campylobacter jejuni* and *Campylobacter coli* in retail meats." *J. Food Prot.* 48: 595-599.

36. Varga, J., B. Mezes, and L. Fodor. 1990. "Serogroups of *Campylobacter jejuni* from man and animal."

37. Wempe, J. M., C. A. Genigeorgis, T. B. Farver, and H. I. Yusufri. 1983. "Prevalence of *Campylobacter jejuni* in two California chicken processing plants." *Appl. Environ. Microbiol.* 45: 355-359.

What is claimed is:

1. An anti-*Campylobacter jejuni* colonizing poultry feed which is useful for preventing the colonization of *Campylobacter jejuni* in a poultry animal, having dispersed therein, as an active ingredient, an effective amount of at least one cecal-colonizing strain of microorganism to provide anti-Campylobacter activity, wherein the strain is selected from the group consisting of *Klebsiella pneumoniae* strain 23 (ATCC No. 55234), *Citrobacter diversus* strain 22 (ATCC No. 55236), *Escherichia coli* (013:H$^-$) strain 25 (ATCC No. 55235), mutants thereof which retain the ability to produce anti-Campylobacter activity, and mixtures thereof.

2. The poultry feed of claim 1 comprising at least about 100 colony forming units of the microorganism per poultry animal.

3. The poultry feed of claim 1 comprising at least about $10^5$ colony forming units of the microorganism per poultry animal.

4. The poultry feed of claim 1 comprising at least about $10^8$-$10^9$ colony forming units of the microorganism per poultry animal.

5. An anti-*Campylobacter jejuni* colonizing composition comprising an effective amount of at least one cecal-colonizing strain of microorganism to provide anti-Campylobacter activity, said strain producing anti-Campylobacter metabolites, and a carrier, wherein the strain is selected from the group consisting of *Klebsiella pneumoniae* strain 23 (ATCC No. 55234), *Citrobacter diversus* strain 22 (ATCC No. 55236), *Escherichia coli* (013:H$^-$) strain 25 (ATCC No. 55235), mutants thereof which retain the ability to produce anti-Campylobacter activity, and mixtures thereof.

6. The composition of claim 5, wherein the carrier is an aerosol.

7. The composition of claim 5, wherein the cecal-colonizing strain is an active ingredient in a poultry feed material, said strain producing anti-Campylobacter metabolites to provide, upon addition to a poultry feed, a poultry feed producing an effective amount of anti-Campylobacter metabolites to inhibit the colonization of *Campylobacter jejuni* in a poultry animal.

8. The composition of claim 7 comprising at least about 100 colony forming units of the microorganism per poultry animal.

9. The composition of claim 7 comprising at least about $10^5$ colony forming units of the microorganism per poultry animal.

10. The composition of claim 7 comprising at least about $10^8$–$10^9$ colony forming units of the microorganism per poultry animal.

11. A process for inhibiting the colonization of *Campylobacter jejuni* in poultry comprising administering an effective amount of at least one cecal-colonizing strain of microorganism, said strain producing anti-Campylobacter metabolites, wherein the strain is selected from the group consisting of *Klebsiella pneumoniae* strain 23 (ATCC No. 55234), *Citrobacter diversus* strain 22 (ATCC No. 55236), *Escherichia coli* (O13:H−) strain 25 (ATCC No. 55235), mutants thereof which retain the ability to produce anti-Campylobacter activity, and mixtures thereof, and a carrier.

12. The process of claim 11 wherein the at least one cecal-colonizing strain of microorganism utilizes mucin as the sole substrate for growth.

13. The process of claim 11, wherein the strain is administered perorally.

14. The process of claim 11, wherein the strain is administered by aerosol.

15. The process of claim 11, wherein the strain is administered to poultry within 7 days of birth.

16. The process of claim 11, wherein the strain is administered to poultry within 1 day of birth.

17. The process of claim 11, comprising administering at least about 100 colony forming units of the microorganism per poultry animal.

18. The process of claim of claim 11, comprising administering at least about $10^5$ colony forming units of the microorganism per poultry animal.

19. The process of claim 11, comprising administering at least about $10^8$–$10^9$ colony forming units of the microorganism per poultry animal.

20. A process for inhibiting the colonization of *Campylobacter jejuni* in poultry comprising dispensing and delivering a dietary supplement comprising an effective amount of at least one cecal-colonizing strain of microorganism, said strain producing anti-Campylobacter metabolites, wherein the strain is selected from the group consisting of *Klebsiella pneumoniae* strain 23 (ATCC No. 55234), *Citrobacter diversus* strain 22 (ATCC No. 55236), *Escherichia coli* (O13:H−) strain 25 (ATCC No. 55235), mutants thereof which retain the ability to produce anti-Campylobacter activity, and mixtures thereof.

* * * * *